United States Patent
Markowitz et al.

(12)

(10) Patent No.: US 6,284,228 B1
(45) Date of Patent: Sep. 4, 2001

(54) COLOR BLENDING SYSTEM FOR FOUNDATION MAKEUP COMPOSITIONS

(76) Inventors: Dan Markowitz; Laurie Markowitz, both of 28 Overlook Rd., Ardsley, NY (US) 10502

( * ) Notice: Subject to any disclaimer, the term of this patent is extended or adjusted under 35 U.S.C. 154(b) by 0 days.

(21) Appl. No.: 09/304,704

(22) Filed: May 4, 1999

(51) Int. Cl.$^7$ .......................... A61K 7/021; A61K 7/035; A61K 7/00
(52) U.S. Cl. ................. 424/63; 424/401; 424/69
(58) Field of Search .................. 424/401, 63, 69

(56) References Cited

U.S. PATENT DOCUMENTS 6,074,652 * 6/2000 Ishiwatari et al. .
6,123,927 * 9/2000 Ogawa et al. .

OTHER PUBLICATIONS

Harry's Cosmeticology, seventh edition, Chemical Publishing Co., Inc, New York, NY, 1982, pp 314–354.*

* cited by examiner

*Primary Examiner*—Thurman K. Page
*Assistant Examiner*—Amy E Pulliam

(57) ABSTRACT

A color blending system for foundation makeup compositions. The system includes a light component consisting of a white pigment, a first red pigment, and a black pigment; a red component consisting of the white pigment, the first red pigment, a violet pigment and a second red pigment; a green component consisting of the white pigment, a first yellow pigment, a green pigment, and a second yellow pigment; and a dark component consisting of the white pigment, the first red pigment, and the black pigment. Each component may be in the form of an emulsion, powder, liquid or solid. A method of formulating a foundation makeup composition for the skin tone of an individual through use of the color blending system. A user blends a desired amount of each of two or more of the components, thus formulating a foundation makeup composition. An individual user formulates a foundation makeup composition without either professional assistance or additional electronic or other equipment.

16 Claims, No Drawings

COLOR BLENDING SYSTEM FOR FOUNDATION MAKEUP COMPOSITIONS

BACKGROUND OF THE INVENTION

1. Field of the Invention

The present invention relates to a color blending system for foundation makeup compositions.

2. Discussion of the Related Art

The use of foundation makeup compositions in a program of beauty enhancement is known. It is recognized that foundation makeup compositions may be applied to the face and other parts of the body to even skin tone and texture, as well as to obscure pores, imperfections, fine lines, and so forth. Since foundation makeup compositions provide color, the user must select a shade suitable to the user's complexion and coloring.

In spite of the benefits obtained from their use, foundation makeup compositions have been criticized for their limited ability to match skin tones. Since the user's selection is normally made at the point of purchase, the user's subjective decision on selection is rendered more difficult if it must take into account differences in lighting between the point of purchase and other places where the user might go. Moreover, since color and skin characteristics vary greatly among individuals, each person has individualized requirements for cosmetic products in general, and foundation makeup compositions in particular.

A number of companies have sought to provide a means for selecting the customer's optimal color shade. For example, CLINIQUE and CLARION have installed computers at sales counters for use by the customer. Information on color shade, oiliness and other properties of a customer's skin are fed into the computer which then determines the company's most closely matching product.

Custom makeup blending is also offered by two companies, PRESCRIPTIVES (a division of ESTEE LAUDER) and VISAGE (a division of REVLON). This involves an initial evaluation of the subject's skin color, then adjustment by the salesperson of existing finished foundations so as to match the evaluated skin color. There are several disadvantages to this method, including that it is available only from a trained salesperson at a retail outlet, such as a department store, and the number of colors able to be achieved via blending is limited based on the available existing finished foundation colors. On many occasions there is a poor skin color match. Additionally, the process is compromised by possible embarrassment, sales pressure and time constraints.

Conventional systems exist for selecting which cosmetics, including foundation makeup compositions, are determined to be optimal for a particular skin tone. Conventional systems also determine the color of a foundation makeup composition which substantially reproduces the color of a person's skin. Conventional systems further reveal customizing foundation makeup compositions based on an analysis of the tone and other characteristics of a person's skin. Conventional systems do not disclose a system whereby an individual can blend a plurality of pigmented components to arrive at a foundation makeup composition whose color is determined by that individual to be optimal, or desirable, for his/her skin tone. Moreover, conventional systems do not disclose a color blending system for foundation makeup compositions which is able to be employed by an individual without either expensive equipment and/or assistance by trained personnel.

What is needed is a color blending system for foundation makeup compositions which is able to provide a custom color blended foundation makeup composition whose color matches the desired color for an individual. Such a system must be usable by an individual without either professional assistance or additional electronic or other equipment. In addition, the system must be sufficiently adaptable so that the color of the foundation makeup composition can be readily altered by an individual user, to take into consideration such factors as changes in light at various times of day, and changes in skin coloration as the result of exposure to the sun. Further, the system must be sized to be able to be carried by an individual, either on her person or in a carrying case, so as to allow for use of the system by an individual in any location.

Accordingly, the present invention provides a novel color blending system for foundation makeup compositions, containing four pigmented components: a light component, a red component, a green component, and a dark component. The system is able to be blended to provide a custom color blended foundation makeup composition whose color matches the desired color of an individual user.

The present invention also provides a novel color blending system for foundation makeup compositions adapted to be used by an individual to provide a custom color blended foundation makeup composition of desired color without either professional assistance or additional electronic or other equipment. The system is sized to be able to be carried by an individual, either on her person or in a carrying case, thus allowing for use of the system by an individual in any location.

BRIEF SUMMARY OF THE INVENTION

The color blending system for foundation makeup compositions of the present invention includes a light component comprising a white pigment, a first red pigment and a black pigment; a red component comprising the white pigment, the first red pigment, a violet pigment and a second red pigment; a green component comprising the white pigment, a first yellow pigment, a green pigment and a second yellow pigment; and a dark component comprising the white pigment, the first red pigment, the black pigment, the second red pigment and the violet pigment.

The present invention is also directed to a method of formulating a foundation makeup composition the color of which is desired by an individual user for her skin tone by employing the color blending system of the present invention. The red component, green component, light component and dark component of the color blending system can each be blended in the form of an emulsion, powder, solid or liquid. The system is sized to be able to be carried by an individual, either on her person or in a carrying case, thus permitting use of the system by an individual in any location.

BRIEF DESCRIPTION OF THE SEVERAL DRAWINGS

Not applicable.

DETAILED DESCRIPTION OF THE INVENTION

Table I shows a formula for the pigmented aspect of each of the light component, red component, green component and dark component.

TABLE I

| Pigment | Light Component Range/Preferred | Red Component Range/Preferred | Green Component Range/Preferred | Dark Component Range/Preferred |
|---|---|---|---|---|
| $TiO_2$ (white) | 95–99.5%/98–99% | 83–90%/85–88% | 56–60%/56–60% | 35–45%/39–42% |
| $Fe_2O_3$ red | .4–2.5%/0.8–1.6% | 8–11%/8–10% | — | 33–43%/36–40% |
| $Fe_2O_3*H_2O$ yellow | — | — | 24–28%/25–27% | — |
| $Fe_2O_3*FeO$ black | 0.01–0.25%/0.01–0.25% | — | — | 9.6–13.6%/11.2–12.0% |
| $Cr_2O_3$ green | — | — | 13–16%/13–16% | — |
| Manganese Violet | — | .5–2.5%/0.8–1.6% | — | 1.4–4%/2.6–3.0% |
| D&C Lake Red 30 | — | 2–5%/2.5–3.5% | — | 5–9%/6.7–7.1% |
| D&C Lake Yellow 5 | — | — | 0.05–0.2%/0.05–0.2% | — |

It will be understood that each of the light, red, green and dark components of the color blending system of the present invention may include additional substances commonly found in foundation makeup compositions. These components can be formulated into any foundation makeup vehicles and/or variations including, for example, any of the numerous conventional foundation makeup vehicles commonly used. Foundation makeup compositions in the form of an emulsion include, in addition to a pigment-containing aspect, complexing agents, silicone oil, humectants, matte finishing agents, emollients, and deionized water. Foundation makeup compositions in the form of a powder include, in addition to a pigment-containing aspect, talc, and sebum absorbing material. Foundation makeup compositions in the form of a solid include, in addition to a pigment-containing aspect, polyoxyalkylene modified organosiloxanes, and cosmetically-acceptable oils. Indeed, the overall formulations of pigment-containing foundation makeup compositions in the forms of an emulsion, a powder and a solid are known and discussed in U.S. Pat. No. 5,871,754 (Briggs et al.), U.S. Pat. No. 5,853,712 (Langlois), U.S. Pat. No. 5,688,831 (El-Nokaly et al.), and U.S. Pat. No. 4,988,503 (Macchio et al.) (emulsion); U.S. Pat. No. 5,683,706 (LaFleur et al.) and U.S. Pat. No. 5,578,311 (Nagatani et al.) (powder); and U.S. Pat. No. 5,681,551 (Nojima)(solid); and each incorporated by reference herein. Such formulations and vehicles may be used for the present invention.

Foundation makeup compositions in the form of an emulsion are prepared by first segregating the various constituent elements into separate groups, based on chemical properties, slowly mixing most of the grouped elements together, heating the resultant mixture, partially cooling the mixture prior to addition of another group of constituent elements, then cooling the resultant mixture further before adding the last groups of constituent elements. The total mixture is then milled. Foundation makeup compositions in the form of a power are prepared by mixing all the dry ingredients together until homogeneous, pulverizing this mixture, separately mixing together the liquid ingredients, and spraying the liquid mixture onto the powdery mixture, followed by further mixing. Foundation makeup compositions in the form of a solid are prepared by dissolving the wax and oil ingredients under heat, adding the pigmented ingredients, casting the resultant mixture into a mold, then charging the cooled mixture into a container.

Methods of preparing foundation makeup compositions in the form of an emulsion, a powder, and a solid are also known and discussed in U.S. Pat. No. 5,871,754 (Briggs et al.), U.S. Pat. No. 5,853,712 (Langlois), U.S. Pat. No. 5,688,831 (El-Nokaly et al.), and U.S. Pat. No. 4,988,503 (Macchio et al.) (emulsion); U.S. Pat. No. 5,683,706 (LaFleur et al.) and U.S. Pat. No. 5,578,311 (Nagatani et al.) (powder); and U.S. Pat. No. 5,681,551 (Nojima) and U.S. Pat. No. 5,317,712 (Ono et al.)(solid); and each is incorporated by reference herein. These teachings may be applied to the present invention as concerns the method of preparing foundation makeup composition.

The color blending system of the present invention specifically excludes beige, tan and/or flesh tone pigments. The four tinted components of the system are novel in their capacity to be blended with each other to produce flesh tones using approved FD&C and DC-grade pigments.

In one embodiment of the color blending system for foundation makeup compositions of the present invention, the amount of white pigment is different in each of the four components. In another embodiment, the amount of the first red pigment is different in each of the light component, the red component and the dark component. In yet another embodiment, the amount of the black pigment is different in the light component as compared to the dark component. In still another preferred embodiment, the white pigment is $TiO_2$. In yet embodiment, the first red pigment is a red iron oxide. In a still further embodiment, the black pigment is a black iron oxide. In still another embodiment, the violet pigment is Manganese Violet. In yet another embodiment, the second red pigment is a D&C Lake Red pigment. In still a further embodiment, the first yellow pigment is a yellow iron oxide. In a still further embodiment, the green pigment is selected from the group consisting of $Cr_2O_3$ green; $Cr_2O_3*H_2O$; ferric ammonium ferrocyanide blue plus a yellow; and Ultramarine Blue plus a yellow. In a still further embodiment, the second yellow pigment is a D&C Lake Yellow pigment.

The color blending system of the present invention may be understood to be modeled after the color wheel notion of complementary colors. Yellow pigments (e.g., yellow iron oxides, D&C Lake Yellow No. 5, D&C Lake Yellow No. 6) and green pigments (e.g., chromium oxides, ferric ammonium ferrocyanide blue plus a yellow, Ultramarine Blue plus a yellow) with white pigment (e.g., titanium dioxide) are blended to form the green component; violet pigments (e.g., Manganese Violet) and red pigments (e.g., red iron oxides, D&C Lake Red No. 9, D&C Lake Red No. 21, D&C Lake Red No. 27, D&C Lake Red No. 13, D&C Lake Red No. 7, D&C Lake Red No. 6, D&C Lake Red No. 30 and D&C Lake Red No. 3) with white (titanium dioxide) are blended to form the red component. Orange and blue pigments are avoided as they are not contained in skin tones. Blending the red component with the green component yields flesh tones without actually necessitating the use of a beige or flesh tone pigments. The light and dark components of the color blending system of the present invention permit the red-green blended flesh tone to be lightened or darkened, respectively, depending on what is desired by the user. Numerous flesh tone hues can be created by varying mixing proportions of complimentary red and green components. The value of the hue can be controlled by selecting between the light, red and dark components.

It is preferable that the green component be used in all blending. In a preferred embodiment, no individual skin tone will require both the light component and the dark component simultaneously; therefore, the color blending system of the present invention may be viewed as two sets of three components—red component, green component, and light component; red component, green component, and dark component—rather than one set of four components. It will be understood, however, that an individual user may blend and two or more (up to and including all four) of the pigmented components of the color blending system of the present invention Each of the four components of the color blending system of the present invention may be present in the form of either an emulsion, a powder or a solid.

The color blending system of the present invention is sized to be able to be carried by an individual, either on her person or in a carrying case, such as a handbag, a purse, a backpack, a pocketbook or a makeup kit, thus permitting use of the system by an individual in any location.

The color blending system of the present invention may be used to yield a custom blended foundation makeup composition as follows: the user blends together an amount of the red component with an amount of the green component. The user may adjust the amounts of either or both of these components based on the user's individual preference. That is, each user will determine amounts of red component and green component desirable for her skin color. To this blend, the user will then blend an amount of either the light component or the dark component, depending on whether the initial red-green blend is too dark or too light, respectively. As noted, however, an individual user may blend any two or more (up to all four) of the pigmented components. The blending of the components may occur in or on any medium, or directly on the skin.

It is understood that the blending of the various components will necessarily be done on a trial-and-error basis, at least initially. However, as the user becomes familiar with the system, custom blending will involve less time and effort. It is understood, as well, that the individual user may prepare at a single blending an amount of custom blended foundation makeup composition sufficient to last for a period of time extending over several days or weeks.

One of ordinary skill in the art will understand that the color blending system of the present invention, when used in accordance with the method of the present invention, permits the formulation of custom blends of foundation makeup compositions in a wide range of colors, able to match a wide range of skin colors.

While the invention has been described with respect to certain specific embodiments, it will be appreciated that many modifications and changes may be made by those skilled in the art without departing from the invention. It is intended, therefore, by the appended claims to cover all such modifications and changes as may fall within the true spirit and scope of the invention.

Sequence Listing
Not Applicable.
What is claimed is:

1. A color blending system for foundation makeup compositions comprising:
   a. a light component comprising:
      i. 95–99.5% $TiO_2$;
      ii. 0.4–2.5% of a red iron oxide; and
      iii. 0.01–0.25% of a black iron oxide;
   b. a red component comprising:
      i. 83–90% $TiO_2$;
      ii. 8–11% of a red iron oxide;
      iii. 0.5–2.5% Manganese Violet; and
      iv. 2–5% of a D&C Lake Red; and
   c. a green component comprising:
      i. 54–62% $TiO_2$;
      ix. 24–28% of a yellow iron oxide;
      x. 13–16% of a chromium oxide green; and
      xii. 0.05–0.2% of a D&C Lake Yellow.

2. The color blending system of claim 1, further comprising a dark component comprising:
   i. 35–45% $TiO_2$;
   ii. 33–43% of a red iron oxide;
   iii. 9.6–13.6% of a black iron oxide;
   iv. 1.4–4% Manganese Violet; and
   v. 5–9% of a D&C Lake Red.

3. A color blending system for foundation makeup compositions comprising:
   a. a red component comprising:
      i. 83–90% $TiO_2$;
      ii. 8–11% of a red iron oxide;
      iii. 0.5–2.5% Manganese Violet; and
      iv. 2–5% of a D&C Lake Red; and
   b. a green component comprising:
      i. 54–62% $TiO_2$;
      ix. 24–28% of a yellow iron oxide;
      x. 13–16% of a chromium oxide green; and
      xii. 0.05–0.2% of a D&C Lake Yellow; and
   c. a dark component comprising:
      i. 35–45% $TiO_2$;
      ii. 33–43% of a red iron oxide;
      iii. 9.6–13.6% of a black iron oxide;
      iv. 1.4–4% Manganese Violet; and
      v. 5–9% of a D&C Lake Red.

4. A method of formulating a foundation makeup composition for a skin tone of an individual, by blending two or more of the components of the color blending system of claim 1, wherein one of said components is said green component.

5. A method of formulating a foundation makeup composition for a skin tone of an individual, by blending two or more of the components of the color blending system of claim 3, wherein one of said components is said green component.

6. The method of claim 4 or claim 5, wherein said color blending system is sized to be able to be carried by an individual, either on her person or in a carrying case, to permit use of said system by an individual in any location.

7. The method of claim 6, wherein said carrying case is selected from a group consisting of a purse, a pocketbook, a handbag, a backpack and a makeup kit.

8. The method of claim 4 or claim 5, wherein each of said components of said color blending system is blended in a form selected from the group consisting of an emulsion, a liquid, a powder and a solid.

9. A color blending system for foundation makeup compositions comprising:
a. a light component comprising:
  i. 98–99% $TiO_2$;
  ii. 0.8–1.6% $Fe_2O_3$ red; and
  iii. 0.01–0.25% $Fe_2O_3$*FeO black;
b. a red component comprising:
  i. 85–88% $TiO_2$;
  ii. 8–10% $Fe_2O_3$ red;
  iii. 0.8–1.6% Manganese Violet; and
  iv. 2.5–3.5% D&C Lake Red 30; and
c. a green component comprising:
  i. 56–60% $TiO_2$;
  ix. 25–27% $Fe_2O_3$*$H_2O$ yellow;
  x. 13–16% $Cr_2O_3$ green; and
  xii. 0.05–0.2% D&C Lake Yellow 5.

10. The color blending system of claim 9, further comprising a dark component comprising:
  i. 39–42% $TiO_2$;
  ii. 36–40% $Fe_2O_3$ red;
  iii. 11.2–12.0% $Fe_2O_3$*FeO black;
  iv. 2.6–3.0% manganese violet; and
  v. 6.7–7.1% D&C Lake Red 30.

11. A color blending system for foundation makeup compositions comprising:
a. a red component comprising:
  i. 85–88% $TiO_2$;
  ii. 8–10% $Fe_2O_3$ red;
  iii. 0.8–1.6% Manganese Violet; and
  iv. 2.5–3.5% D&C Lake Red 30;
b. a green component comprising:
  i. 56–60% $TiO_2$;
  ix. 25–27% $Fe_2O_3$*$H_2O$ yellow;
  x. 13–16% $Cr_2O_3$ green; and
  xii. 0.05–0.2% D&C Lake Yellow 5; and
c. a dark component comprising:
  i. 39–42% $TiO_2$;
  ii. 36–40% $Fe_2O_3$ red;
  iii. 11.2–12.0% $Fe_2O_3$*FeO black;
  iv. 2.6–3.0% manganese violet; and
  v. 6.7–7.1% D&C Lake Red 30.

12. A method of formulating a foundation makeup composition for a skin tone of an individual, by blending two or more of the components of the color blending system of claim 9 wherein at least one of said components is said green component.

13. A method of formulating a foundation makeup composition for a skin tone of an individual, by blending two or more of the components of the color blending system of claim 11 wherein at least one of said components is said green component.

14. The method of claim 12 or claim 13, wherein said color blending system is sized to be able to be carried by an individual, either on her person or in a carrying case, to permit use of said system by an individual in any location.

15. The method of claim 14, wherein said carrying case is selected from a group consisting of a purse, a pocketbook, a handbag, a backpack and a makeup kit.

16. The method of claim 12 or claim 13, wherein any of said components of said color blending system is blended in a form selected from the group consisting of an emulsion, a liquid, a powder and a solid.

* * * * *